United States Patent [19]
Anami

[11] Patent Number: 5,525,298
[45] Date of Patent: Jun. 11, 1996

[54] APPARATUS FOR TAKING LIQUID CONTENT FOR USE IN ANALYSIS OUT OF CONTAINER

[75] Inventor: Takayuki Anami, Iruma, Japan

[73] Assignee: Olympus Optical Co., Ltd., Tokyo, Japan

[21] Appl. No.: 337,189

[22] Filed: Nov. 7, 1994

Related U.S. Application Data

[63] Continuation-in-part of Ser. No. 868,878, Apr. 16, 1992, Pat. No. 5,380,486.

[30] Foreign Application Priority Data

| Apr. 19, 1991 | [JP] | Japan | 3-113786 |
| Apr. 19, 1991 | [JP] | Japan | 3-113787 |

[51] Int. Cl.$^6$ ..................................................... G01N 21/01
[52] U.S. Cl. ...................... 422/63; 422/64; 422/65; 422/69; 422/99; 422/81; 422/100; 436/49; 436/54; 436/174; 436/177; 436/180; 73/863.01; 73/863.85; 73/864.21; 73/864.22; 73/864.25; 73/864.24
[58] Field of Search ................. 73/863.01, 863.85, 73/864.21, 864.22, 864.24, 864.25; 422/63, 64, 65, 69, 99, 100, 81; 436/174, 177, 180, 54, 49

[56] References Cited

U.S. PATENT DOCUMENTS

| 3,178,266 | 4/1965 | Anthon | 23/253 |
|---|---|---|---|
| 3,748,911 | 7/1973 | Rousselet et al. | 73/863.01 |
| 3,872,730 | 3/1975 | Ringrose et al. | 73/421 B |
| 3,894,438 | 7/1975 | Ginsberg | 73/423 A |
| 3,901,656 | 8/1975 | Durkos et al. | 23/230 B |
| 3,994,687 | 11/1976 | Engelbrecht | 23/230 R |
| 4,056,981 | 11/1977 | Kalka et al. | 73/863.85 |
| 4,063,460 | 12/1977 | Svensson | 436/174 |
| 4,217,798 | 8/1980 | McCarthy et al. | 81/3.2 |
| 4,454,234 | 6/1984 | Johnson | 436/180 |
| 4,475,411 | 10/1984 | Wellerfors | 73/864.24 |
| 4,478,095 | 10/1984 | Bradley et al. | 73/864.21 |
| 4,522,089 | 6/1985 | Alvi | 81/3.42 |
| 4,558,603 | 12/1985 | Chlosta et al. | 73/864.21 |
| 4,577,514 | 3/1986 | Bradley et al. | 73/863.01 |

(List continued on next page.)

FOREIGN PATENT DOCUMENTS

| 0452892 | 10/1991 | European Pat. Off. . |
| 257819 | 6/1988 | German Dem. Rep. . |
| 2312010 | 9/1973 | Germany . |
| 2508704 | 8/1976 | Germany . |
| 2640036 | 3/1978 | Germany . |
| 2907558 | 8/1980 | Germany . |
| 3614954 | 11/1987 | Germany . |
| 403526 | 11/1965 | Switzerland . |

*Primary Examiner*—Jill Warden
*Assistant Examiner*—Sharidan Carrillo
*Attorney, Agent, or Firm*—Watson Cole Stevens Davis

[57] ABSTRACT

A device for delivering a serum sample from a blood collection tube into one or more sample vessels or reaction vessels, including a pair of arms which are arranged movably in opposite directions, a motor for driving the arms to selectively grasp the blood collection tube, a block to which the arms are provided, a motor for rotating the block over 135 degrees, a needle-like suction nozzle secured to the block, a syringe having a main body coupled with the suction nozzle and a piston arranged movably within the main body, a motor for driving a piston of the syringe, a slide block on which the block is arranged rotatably, a motor for moving the slide block in right and left directions, a base member arranged movably up and down, and a motor for driving the base member up and down. After the blood collection tube is picked out of a rack by the arms, the base member is moved downward to insert the suction nozzle into the container through the cap, and then the block is rotated to turn over the blood collection tube. Then, the serum sample is sucked by operating the syringe, and then the block is rotated into an initial position. After the suction nozzle is pulled out of the cap, a given amount of the sucked serum sample is discharged into one or more sample vessels or reaction vessels.

22 Claims, 9 Drawing Sheets

U.S. PATENT DOCUMENTS

| | | | |
|---|---|---|---|
| 4,803,050 | 2/1989 | Mack | 422/65 |
| 4,811,611 | 3/1989 | Offenheimer | 73/864.22 |
| 4,815,325 | 3/1989 | Averette | 73/864.21 |
| 4,841,818 | 6/1989 | Plapp et al. | 81/3.08 |
| 4,861,553 | 8/1989 | Mawhirt et al. | 422/65 |
| 4,928,539 | 5/1990 | Champseix et al. | 73/864.24 |
| 4,938,929 | 7/1990 | Bost | 422/100 |
| 4,951,512 | 8/1990 | Mazza et al. | 73/861.23 |
| 4,962,041 | 10/1990 | Roginski | 436/150 |
| 4,994,240 | 2/1991 | Hayashi | 422/63 |
| 5,013,529 | 5/1991 | Itoh | 422/100 |
| 5,080,864 | 1/1992 | Shaw | 422/62 |
| 5,130,254 | 7/1992 | Collier et al. | 436/54 |
| 5,151,184 | 9/1992 | Ferkany | 210/514 |
| 5,201,794 | 4/1993 | Kasai et al. | 73/863.01 |
| 5,216,926 | 6/1993 | Lipscomb | 73/863.85 |
| 5,262,049 | 11/1993 | Ferkany | 422/65 |
| 5,270,219 | 12/1993 | DeCastro et al. | 436/180 |
| 5,380,486 | 1/1995 | Anami | 422/63 |

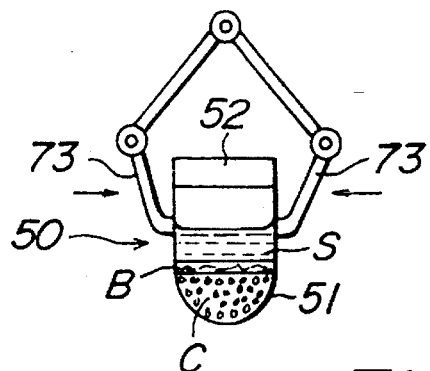
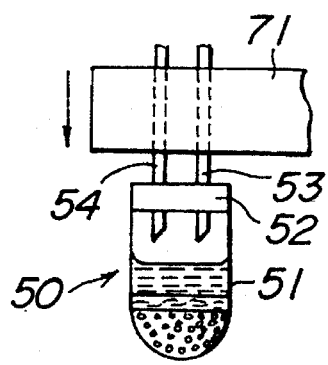
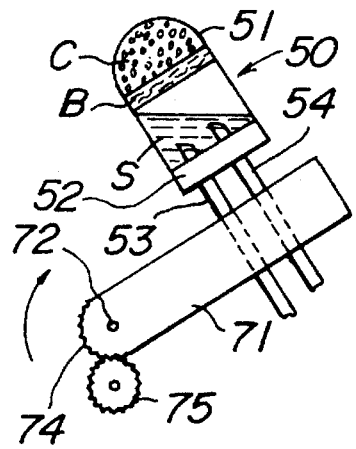
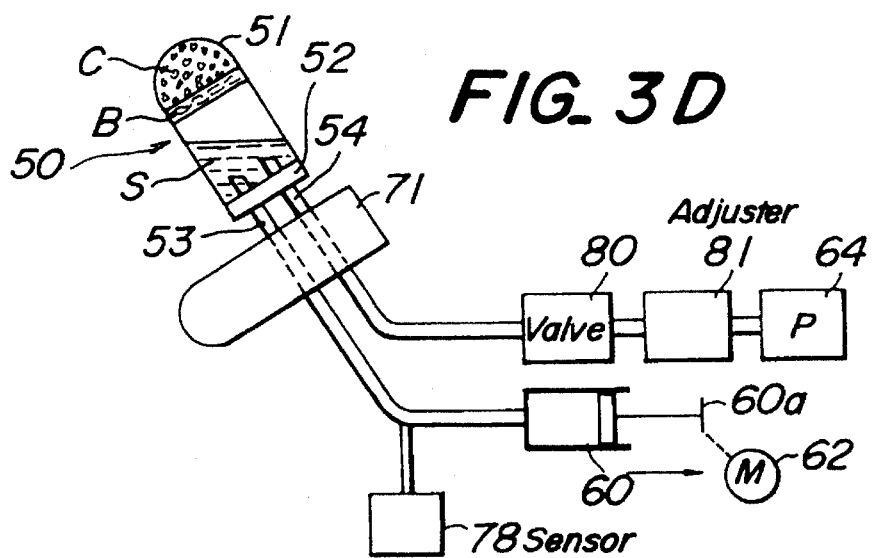

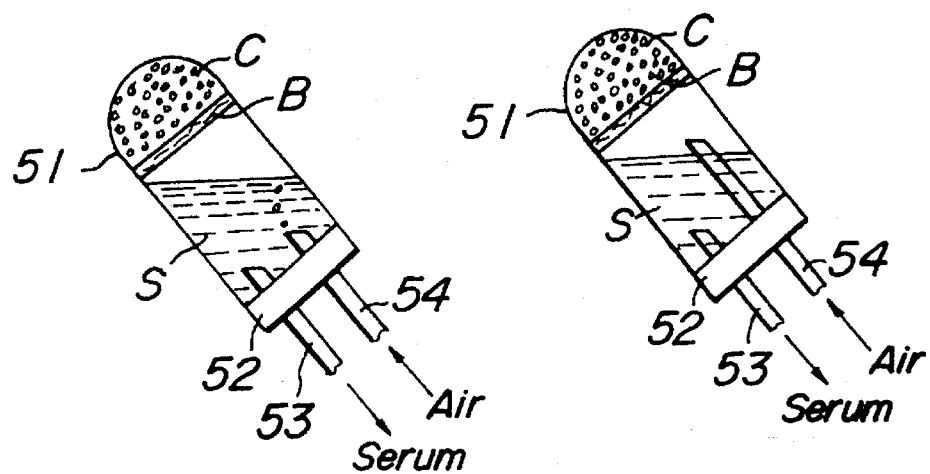

5,525,298

APPARATUS FOR TAKING LIQUID CONTENT FOR USE IN ANALYSIS OUT OF CONTAINER

This is a continuation-in-part application of the U.S. patent application Ser. No. 868,878 filed on Apr. 16, 1992, now U.S. Pat. No. 5,380,486.

BACKGROUND OF THE INVENTION

1. Field of the Invention

The present invention relates to an apparatus for taking a liquid content for use in analysis out of a container including a container main body having an opening and a cap secured hermetically to said opening to keep an inside of the container main body at a reduced or negative pressure.

2. Description of the Related Art Statement

In a chemical or biological analyzing system, a liquid content such as various kinds of samples derived from patients and reagents are usually contained in a container comprising a container main body having an opening and a cap hermetically is secured to the opening to keep the inside of the container main body. In order to store such a liquid content reliably, the liquid content is sometimes dried and dried substances are contained in the container. Upon usage, a solvent is added to form a solution and a given amount of the solution is taken out of the container. Apparatuses for taking a liquid content out of such a container may be roughly classified into the following two types. In a first type, at first the cap is removed from the container main body, and then the liquid content is taken out of the container by inserting the suction nozzle into the container main body via the opening. In a second type of the apparatus, a suction nozzle having a tip in the form of a needle is inserted into the container main body by piercing the needle through the cap made of rubber and the liquid content is sucked into the suction nozzle.

In a blood analyzing system, a sample blood has to be taken out of a patient into a blood collection tube having a rubber cap. When the sample blood is collected from the patient, use is generally made of a vacuum type blood collection tube. In this type of blood collection tube, the inside of the tube is kept at a negative pressure and a sample blood is sucked into the tube effectively. After the sample blood has been sucked into the tube, the inside of the tube is still maintained at a negative pressure. Therefore, when the rubber cap is removed from the blood collection tube in order to take the sample blood out of the blood collection tube, the pressure inside the tube is abruptly increased from the negative pressure to the atmospheric pressure, so that the sample blood might be spread or overflowed from the tube. Then, an amount of the blood sample remained in the tube becomes small and a given amount of the sample blood could not be taken out. In this connection, it should be noted that nowadays test items to be analyzed for the sample blood has become larger, so that the collected blood sample has to used efficiently. Thus, when a part of the collected blood sample is overflowed from the blood collection tube, all the test items to be denoted for the sample blood could be no more performed. Moreover, since the pressure inside the tube varies during the operation for removing the rubber cap from the tube, control of a force for performing a punctual removal of the rubber cap in a determined time becomes very complex.

When the blood sample is taken out of the blood collection tube without removing the rubber cap, the suction nozzle having a needle secured to its distal end is inserted into the tube through the rubber cap such that the tip of the needle is immersed into the sample blood. After a given amount of the blood sample has been sucked into the suction nozzle, when the needle is removed out of the tube, an air is sucked into the needle, because the inside of the blood collection tube is maintained at the negative pressure. When the air is sucked into the needle and often makes undesired bubbles in the blood, an amount of the blood sample which is delivered from suction nozzle into a reaction vessel becomes smaller than a desired amount and the accuracy of the analysis is affected. Further, when the blood sample is sucked into the suction nozzle, the pressure inside the blood collection tube is reduced, and thus the control of the suction force for maintaining the accuracy of suction constantly becomes complicated.

When a serum of a sample blood is taken out of the vacuum type blood collection tube, the blood collection tube having the sample blood sucked therein is first set into a centrifugal apparatus and a serum and blood cells of the sample blood are separated from each other. Usually a separating agent mainly consisting of silicon is added to the blood sample. That is to say, the blood cells are collected into a lower portion of the tube as a clot and the serum is existent on the clot of blood cells. In order to take a given amount of the serum sample out of the tube, a suction nozzle is inserted into the tube through the rubber cap such that a tip of the serum sample sucking nozzle is immersed into the serum. However, a position of the tip of the suction nozzle in the serum is rather critical. When the suction nozzle is immersed into the serum deeply, undesired blood cells and separating agent might be sucked into the suction nozzle. Further the sucked blood cells and separation agent might clog the suction nozzle. On the contrary, when the suction nozzle is not sufficiently immersed into the serum, an amount of the sucked serum becomes smaller than a required amount. Moreover, an air might be introduced into the suction nozzle. Therefore, the suction nozzle has to be immersed into the serum such that its tip comes closer to a boundary between the clot and the serum. However, the position of the boundary between the clot and the serum varies for respective blood samples, so that it is necessary to detect the boundary. To this end, an assembly of a light source for emitting light and a photodetector for receiving the light emitted from the light source and transmitted through the blood collection tube is moved along a longitudinal axis of the tube. There is further proposed to use a sensor for detecting the position of the boundary by using light reflected by the boundary. However, usually on an outer surface of the blood collection tube there are provided a label on which patient number, identification number, patient name and so on are recorded and a bar code label. Sizes and positions of these labels on the tube differ widely from tube to tube. In some cases, a label is adhered around an entire surface of the tube. Therefore, it is very difficult to detect reliably the position of the boundary between the clot and the serum.

In order to detect the position of the boundary, there has been further proposed to measure an electrostatic capacitance or an electric resistance between electrodes which are secured to the tip of the suction nozzle and are immersed into the blood sample. However, such an electrical detection could not be performed reliably.

FIG. 1 shows a known apparatus for removing a rubber cap from an opening of a vacuum type blood collection tube. The apparatus comprises holding arms 2 for holding a vacuum type blood collecting tube 1 having an upper opening which is closed by a rubber cap 3 in a hermetical manner. The apparatus further comprises cap removing arms 4 which are arranged movably in a horizontal direction as well as in the vertical direction. On distal ends of the cap removing arms 4 there are secured pins 5 directing inwardly. After the tube 1 is grasped by the arms 2, the cap removing arms 4 are moved horizontally to come closer to each other and the pins 5 are penetrated into the rubber cap 3. Then, the cap removing arms 4 are moved upward to remove the rubber cap 3 from the tube opening. However, as stated above, the inside of the tube 1 is kept at the negative pressure, it is rather difficult to remove the rubber cap 3 only by moving the removing arms 4 upward. Therefore, an assembly of the cap removing arms 4 is arranged to be swingable about an axis which extends vertically to a plane of the drawing of FIG. 1 by means of any suitable swinging mechanism. When the cap removing arms 4 are swung, the rubber cap 3 is deformed to form a thin space between the cap and the tube so that an air is introduced into the tube 1 and the pressure inside the tube is gradually increased. In this manner, the rubber cap 3 can be removed from the blood collection tube 1.

In the known rubber cap removing apparatus shown in FIG. 1, it is necessary to swig the assembly of the cap removing arms 4, and this requires a very complicated swinging mechanism. Further when the tube 1 is made of glass, the tube is liable to be broken by the swinging movement.

Further, in the known apparatus, the pins 5 are inserted into the rubber cap 3, so that this apparatus could not be applied to other tubes which is made of other material or which is formed in different shapes.

In the chemical or biological analyzing system, the hermetically sealed container is generally vacuumed in order to avoid the evaporation of liquid substances, the oxidation of liquid or dried solid substances and the moisture absorption of dried substances. The dried substances are forming the powders by removing water and are stored in the container. When such dried substances are used, suitable solvent is supplied into the container to form a solution. Then a given amount of the solution is taken out of the container by either one of the above explained two methods. Such dried substances are enzymes, antigens and antibodies.

Further, the pressure inside the container may be reduced by providing the cap under the reduced pressure or by keeping the container at a low temperature after the cap is provided in the atmospheric pressure. In order to keep the reduced pressure reliably, a sealing member may be provided or the cap may be screwed into the opening of the container main body.

The container main body may be formed in any desired shape and the size of the opening should be sufficiently wide for introducing the suction nozzle into the container main body through the opening. The container main body may be made of any desired material which has a substantially hermetic property in accordance with chemical and physical properties, environments under which the container is kept and the frequency of usages. The cap should be made of material which has a substantially hermetic property and which affords the piercing of the suction nozzle. Usually the cap is made of natural or synthetic rubbers for being elastically pushed into an opening of the container, or plastics such as polystyrene or polyethylene having a screw structure with the container. In case of taking liquid contents from these containers, the above mentioned problems would equally occur.

There has been proposed another type of liquid taking apparatus in which a liquid can be taken out of a container without removing a cap. For instance, U.S. Pat. No. 4,928,539 to Champseix is directed to a device for automatically taking liquid from a bottle, which includes a rotary dispenser holding a plurality of liquid sample containing tubes to turn over one by one and a piercing assembly positioned below the rotary dispenser. The piercing assembly includes a sample taking needle which can move up and down and a pipe whose one end is connected with the needle and whose other end extends under the tube to allow transfer of the fluid sample taken. Herein the needle is moved upward to pierce the tube which is inverted by 180° with respect to the upright position.

U.S. Patent to Ferkany is directed to a fluid collecting and dispensing system, which includes a table having a gripper for releasibly locking a plurality of liquid sample containing tubes in inverted position therein and a sample collection station positioned below the tubes. The sample collection system includes fluid-extraction needle which can move up and down and can rotate by 180° between a position pointing upward below the inverted tube being held on a conveyer and a position pointing downward above a sample receiving vessel. Herein, the tubes are manually loaded onto the conveyer in inverted posture which is 180° with respect to the upright posture.

SUMMARY OF THE INVENTION

The present invention has for its object to provide a novel and useful apparatus for taking a liquid content for use in analysis out of a container which includes a container main body having an opening and a cap which is hermetically secured to said opening to keep an inside of the container main body at a reduced pressure, in which a desired amount of the liquid content can be taken precisely without being influenced by the reduced pressure within the container main body.

It is another object of the invention to provide an apparatus for taking a liquid content for use in analyses from a container which includes a container main body having an opening and a cap which is hermetically secured to the opening, in which the liquid content can be sucked effectively without performing any liquid level detection.

According to the invention, an apparatus for taking a liquid content for use in analysis out of a container, the container including a container main body having an opening and a cap which is hermetically secured to the opening to keep an inside of the container main body at an initial pressure, the apparatus comprises:

holding means for detachably holding a container in a normal posture in which the cap is at a top of the container;

liquid content taking means comprising at least a needle-like suction nozzle having a tip which can pierce said cap and a hollow member opened in vicinity of said tip to flow a liquid thereinto;

supporting means for supporting skid liquid content taking means above said holding means and directing the tip of said needle-like suction nozzle downwardly towards said cap, while said container has been held by said holding means;

piercing means for moving said suction nozzle and said holding means approaching and apart each other such that said tip of said suction nozzle is inserted into said cap until the opening of said tip is slightly protruded from a rear surface of said cap into an inner space located between the rear surface of said cap and a level held above a surface of said liquid content, while said container has been held by said holding means, and is pulled out of the container main body through said cap;

rotating means for rotating said supporting means of said liquid content taking means so as to maintain to insert at least said needle-like suction nozzle into said cap, so that said container can be reversibly rotated together with the suction nozzle so as to change said normal posture into a sucking posture in which the container is substantially turned over and said cap is located at a bottom of said container;

transporting means for moving said liquid content taking means at least between a position above the cap of said container being held by said holding means and a position above at least a liquid content receiving vessel;

liquid content sucking and discharging means communicated with said suction nozzle of said liquid content taking means and being operative to suck a required amount of the sample into said suction nozzle and to discharge a given amount of the thus sucked liquid content into at least one of said sample vessel; and control means for controlling at least said piercing means, rotating means, transporting means and liquid content sucking and discharging means.

In the liquid content taking apparatus according to the invention, after the needle-like suction nozzle has been inserted into the container main body through the cap, the container is turned over so that an opening of the suction nozzle can be effectively immersed in the liquid, and thus a given amount of the liquid content can be sucked into the suction nozzle without performing the liquid level detection. Therefore, it is no more necessary to remove a bar code label applied on an outer surface of the container main body in order to perform the liquid level detection using an optical system.

BRIEF DESCRIPTION OF THE DRAWINGS

FIGS. 3A, 3B, 3C and 3D are schematic views depicting the operation of the apparatus illustrated in FIG. 2;

FIGS. 4A and 4B are schematic views representing two embodiments of the assembly of the suction nozzle and air supply nozzle;

DESCRIPTION OF THE PREFERRED EMBODIMENTS

Figure 1:
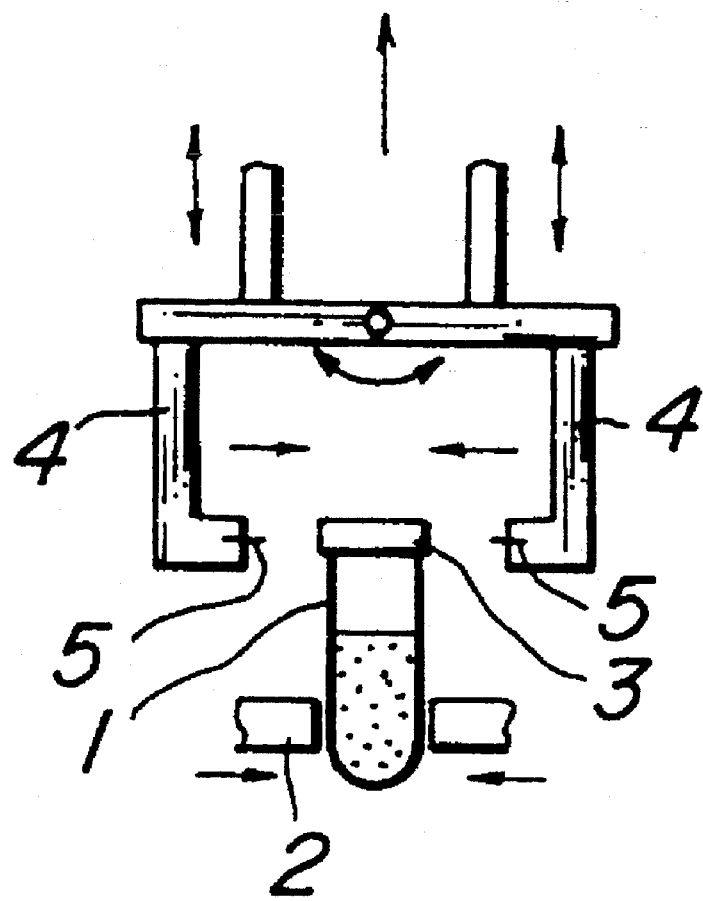
FIG. 1 is a schematic view showing a known apparatus for removing a rubber cap from a container.
Figure 2:
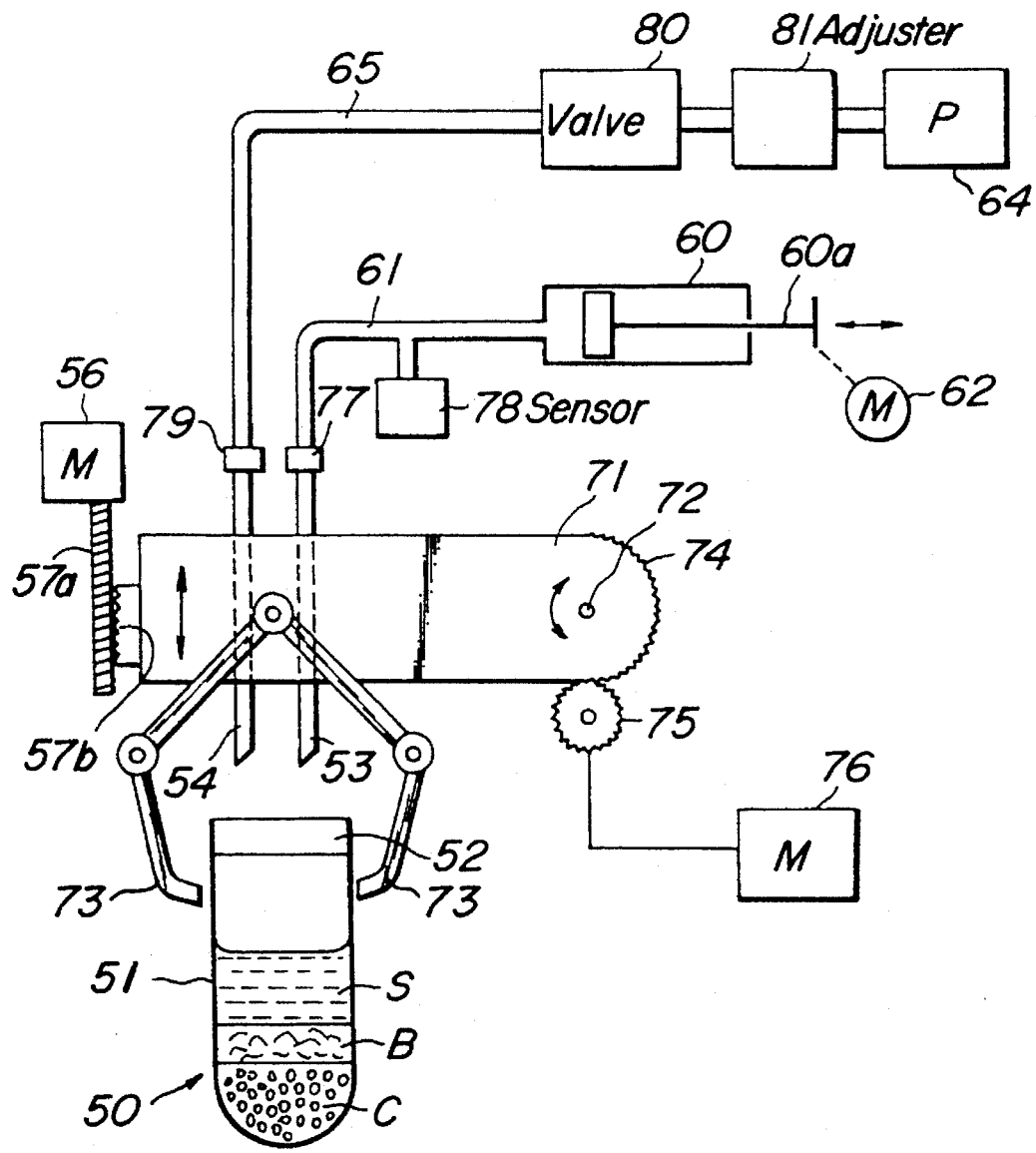
FIG. 2 is a schematic view illustrating an embodiment of the serum sample delivering apparatus according to the invention.

FIG. 2 shows an embodiment of the liquid content taking apparatus according to the invention. In the present embodiment, the apparatus is constructed to take a serum sample out of a blood collection tube. A vacuum type blood collection tube 50 comprises a tube 51 serving as the container main body made of glass or plastics and a rubber cap 52 which is hermetically secured to an upper opening of the tube 51. It should be noted that after a sample blood has been taken from a patient into the tube 51, a needle has been removed from the tube. The pressure inside the tube 51 is kept at a reduced or negative pressure, so that the cap 52 could not be easily removed from the tube 51. Within the tube 51, the sample blood is separated into a serum S and a clot C by means of a boundary layer B. In order to suck the sample serum S reliably, it is generally required to detect a liquid level as well as a level of the boundary layer B. The levels of the serum S and boundary layer B may be optically detected. However, in some cases, it would be difficult to detect the boundary layer B reliably due to a bar code label applied on an outer surface of the tube 51. In the present embodiment, a given amount of the serum can be taken out of the tube 51 without detecting the level of the serum S and boundary layer B.

The apparatus comprises a block 71 which is arranged movably up and down as well as rotatably about a shaft 72. To the block 71 are secured a pair of arms 73 for holding the tube 51. Further a needle-like suction nozzle 53 and a needle-like air supply nozzle 54 both made of hard and rust-proof material such as aluminum, stainless steal, ceramics or the like are secured to the block 71. The cap 52 functions to attain a sealing and is made of rubber or plastics. The cap 52 should be formed such that a tip of nozzle can pierce the cap. The construction of the tip of nozzle and an insertion angle have to be designed such that the nozzle is not clogged. To one side wall of the block 71 there is secured a rack gear 57b which is engaged with a pinion gear 57a secured to an output shaft of an electric motor 56. By energizing the motor 56, the block 71 is moved up and down together with the suction nozzle 53 and air supply nozzle 54.

In the other side wall of the block 71 there is formed a semicircular rack gear 74 which is engaged with a pinion gear 75 which is connected to an output shaft of an electric motor 76. By driving the motor 76, the block 71 is rotated about the shaft 72. It should be noted that the shaft 72, pinion gear 75 and motor 76 are provided on a member which is moved up and down by means of the motor 56. The suction nozzle 53 is coupled with a syringe 60 by means of joint 77 and tube 61 made of polytetrafluoroethylene. To the tube 61 is also connected a pressure sensor 78. The air supply nozzle 54 is coupled with an air compressor 64 by means of joint 79, tube 65 made of polytetrafluoroethylene, air supply rate adjustor 81 and decompression valve 80.

Now the operation of the apparatus shown in FIG. 2 will be explained also with reference to FIG. 3. At first, the rubber cap 52 of the vacuum tube blood collection tube 50 is removed and a separating agent mainly consisting of silicon is added to the sample blood contained in the tube 51. Then, after the rubber cap 52 has been secured to the opening of the tube 51, the tube is set in a centrifugal device to separate the sample blood into the serum S and the clot C, while the boundary layer B is existent therebetween. The blood collection tube 50 is set in a normal posture in which the cap 52 faces upwards. In this normal posture, the tube 50 is held by the arms 73 as depicted in FIG. 3A. Then the motor 56 is energized to move the block 71 downward. During this downward movement of the block 71, tips of the suction nozzle 53 and air supply nozzles 54 pierce through the rubber cap 52 and are inserted into the tube 51 as shown in FIG. 3B to such an extent that tips of these nozzles situate just below a rear surface of the cap. Next, the motor 76 is driven to rotate the block 71 by means of the pinion gear 75 and semicircular rack gear 74 to move the tube 51 into a substantially up-side down position as shown in FIG. 3C. During this rotational movement, only the serum S is moved downward, because the clot C are remained in the bottom portion of the tube 51 by means of the boundary layer B. After that, the syringe 60 is operated to suck a given amount of the serum S into the suction nozzle 53 as depicted in FIG. 3D. At the same time, the air compressor 64 is energized to supply the air into the tube 51 by means of the air supply nozzle 54. Usually the inside of the tube 51 is kept at a negative pressure, and in such a case the air is introduced into the tube 51 such that the original negative pressure and a negative pressure produced by sucking the serum have to be compensated for. The pressure of the air supplied into the tube 52 is controlled by the decompression valve 80 and the air supply rate is controlled by the air supply rate adjuster 81 such that an amount of the air supplied into the tube is substantially identical with an amount of the serum S sucked into the suction nozzle 53. The suction of the serum S into the suction nozzle 53 is controlled by monitoring the pressure inside the tube 51 by the sensor pressure 78. When it is detected that the tip of the suction nozzle 53 is going to extend above a liquid level of the serum S, the suction is stopped so that an air is not introduced into the suction nozzle.

After a given amount of the serum S has been sucked into the suction nozzle 53, the motor 76 is driven in the opposite direction to rotate the block 71 into the initial position. Then, the motor 56 is driven again in the opposite direction to move the block 71 upward to remove the suction nozzle 53 and air supply nozzle 54 from the tube 50. The serum sucked into the suction nozzle 53 is discharged from the tip of the suction nozzle into a suitable reaction vessels by moving the piston rod 60a in the opposite direction.

In the above explained embodiment shown in FIG. 2, the tips of the suction nozzle 53 and air supply nozzle 54 are inserted into the tube 51 up to the substantially same level as illustrated in FIG. 4A. Therefore, the tip of the air supply nozzle 54 is in the serum S and the air is introduced into the tube 51 in the form of air bubbles. Then, the air bubbles might be sucked into the suction nozzle 53, and therefore an amount of the serum sucked into the suction nozzle becomes smaller than a desired amount. In order to avoid such a drawback, according to the invention a tip of an air supply nozzle 54 may be deeply inserted into the tube 51 such that the tip of the air supply nozzle protrudes above a liquid level of the serum S as shown in FIG. 4B.

Figure 5:
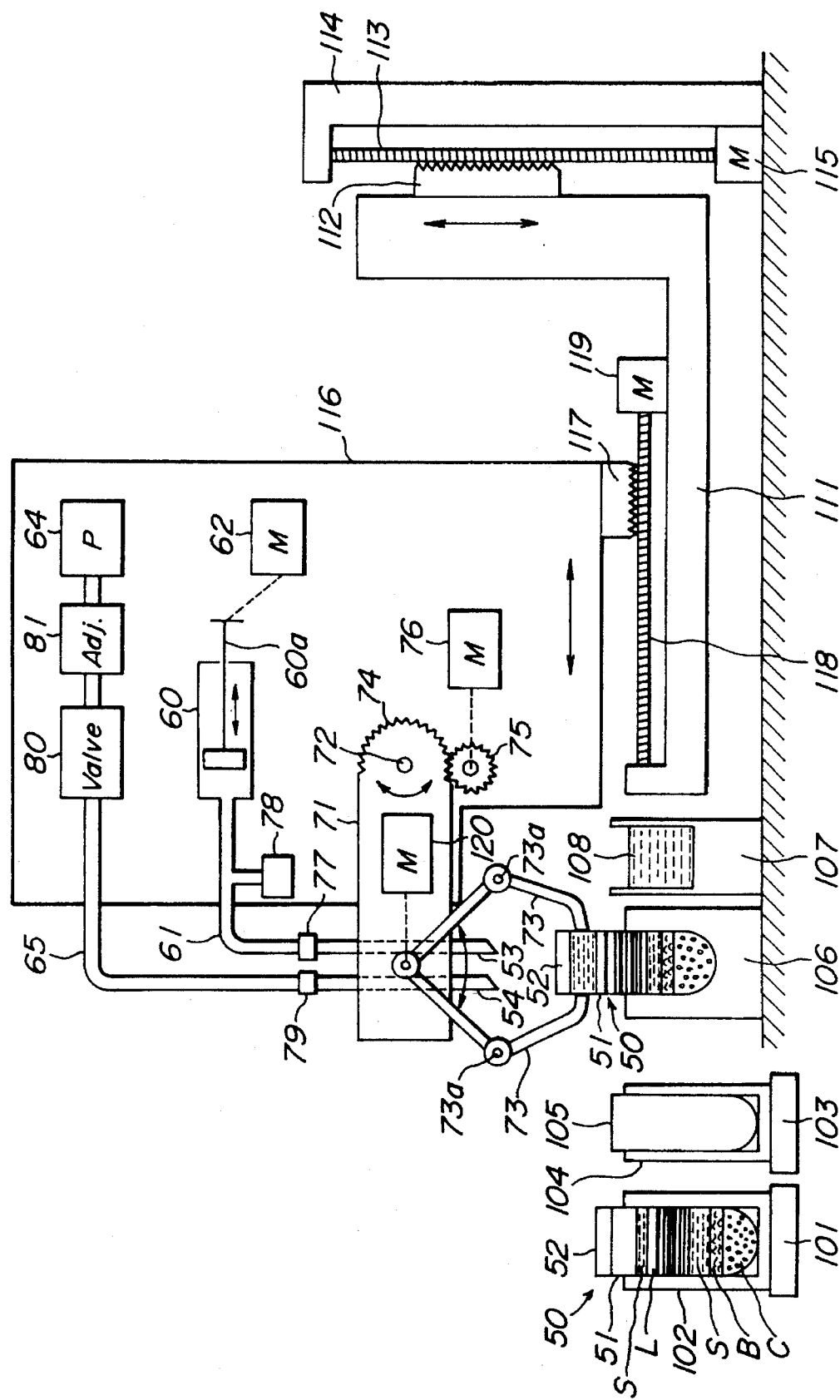
FIG. 5 is a schematic view showing another embodiment of the serum sample delivering apparatus according to the invention.

FIG. 5 is a schematic view illustrating a second embodiment of the serum sample delivery device according to the invention. In the present embodiment, portions similar to those of the first embodiment shown in FIG. 2 are denoted by the same reference numerals used in FIG. 2. There is provided a blood collection tube feeding means 101 for transporting a plurality of first racks 102 each detachably holding a plurality of blood collection tubes 50 toward a pick-up position one by one along a blood collection tube feeding path extending in a direction which is perpendicular to the plane of the drawing of FIG. 5. It should be noted that said pick-up position is in the plane of the drawing of FIG. 5. At an upstream position of the feeding path of the feeding means 101 with respect to the pick-up position, there is arranged a device for automatically or manually setting the blood collection tubes 51.

Each of the blood collection tubes 50 comprises a container main body 51 having an opening and a rubber cap 52 which is hermetically secured to the opening of the container main body 51. On an outer surface of the container main body 51, there is applied a bar code label L on which there are recorded various kinds of information such as patient code and test items to be performed for a relevant sample blood. Between the above mentioned blood collection tube setting means and the pick-up position viewed along the feeding path of the feeding means 101, there is provided a conventional bar code reader not shown for reading the bar code label L applied on the blood collection tube 51, so that before a blood collection tube 51 has arrived at the pick-up position, a bar code label L applied on the relevant blood collection tube 51 is read out and a read out signal is applied to a control unit such as CPU not shown. Within the container main body 51, there are contained serum S and clot C separated by a boundary layer B.

There is further arranged a sample vessel feeding means 103 for feeding a plurality of second racks 104 each detachably holding a plurality of sample vessels 105 in parallel with the blood collection tube feeding path. There are provided a third rack 106 for detachably holding a blood collection tube 50 and a washing vessel 107 containing a washing liquid 108 for washing sample suction nozzle and air supply nozzle.

The sample delivery apparatus of the present embodiment further comprises a base member 111 which is arranged movably up and down. On a side wall of the base member 111 is secured a rack gear 112 which is engaged with a screw shaft 113 arranged rotatably to a post member 114. A lower end of the screw shaft 113 is secured to an output shaft of a first motor 115. When the first motor 115 is driven in a first direction, the screw shaft 113 is rotated in a first direction and the base member 111 is moved upward. When the first motor 115 is driven in a second direction, the base member 111 is moved downward. An amount o the up-down movement of the base member 111 is determined such that the container can be removed from the racks 101 and 106 and the needle-like nozzles 53 and 54 can completely pierce the cap 52. On the base member 111 there is arranged a slide member 116 movably in right and left directions, and a rack gear 117 is provided on a bottom of the slide member 116, which is engaged with a second screw shaft 118 arranged horizontally so that said arms 73 can reach above said first rack 102, second rack 104, third rack 106 and washing vessel 107. One end of the second screw shaft 118 is coupled with an output shaft of a second motor 119 arranged on the base member 111. When the second motor 119 is driven in a first direction, the slide member 116 is moved leftward, and when the second motor 116 is driven in a second direction, the slide member 116 is moved rightward.

On the slide member 116 there is provided a rotating block 71 which is arranged rotatably about to a shaft 72 secured to the slide member 116. In a side wall of the block 71 there is formed a semicircular rack gear 74 which is engaged with a pinion gear 75 which is coupled with a third motor 76. By driving the third motor 76 in a first direction, the block 71 is rotated in the clockwise direction, and by driving the third motor in a second direction, the block is rotated in the counter-clockwise direction. Thus, the rotating block 71 reversibly rotates between a first position where the blood collection tube 50 makes the normal posture in which the cap 52 is located at a top of the whole blood collection tube 50 and a sucking posture in which the blood collection tube 50 is substantially turned over and the cap 52 is located at a bottom of the blood collection tube 50, while the needle-like suction nozzle 53 and air supply nozzle 54 have been inserted into the cap 52.

In the present embodiment, the needle-like suction nozzle 53 and air supply nozzle 54 are fixed to the block 71. The suction nozzle 53 is coupled with a syringe 60 by means of joint 77 and flexible tube 61 made of polytetrafluoroethylene. A piston 60a of the syringe 60 is coupled with a fourth motor 62. When the fourth motor 62 is driven in a first direction, the piston of the syringe 60 is drawn from a main body of the syringe and when the fourth motor 62 is driven in a second direction, the piston is pushed into the syringe main body. An amount of the movement of the fourth motor 62 can be adjusted by the control unit which receives the output signal of the bar code reader reading the bar code label L on the blood collection tube 50 in accordance with an amount of the blood sample sucked from the blood collection tube, the number of sample vessels into which the sucked sample has to be delivered, and amounts of sample blood delivered into the sample vessels. If the test items read out of the bar code label L requires a plurality of analyzers, the apparatus is preferably controlled by the control unit to deliver the sucked serum sample into a plurality of sample vessels the number of which is equal to that of the analyzers, amounts of serum samples delivered into respective sample vessels corresponding to those which are required in respective analyzers for analyzing one or more denoted test items.

To the tube 61 is connected a pressure sensor 78 for detecting a pressure within the blood collection tube 50. The air supply nozzle 54 is coupled with an air compressor 64 by means of joint 79, flexible tube 65 made of polytetrafluoroethylene, decompression valve 80 and air supply rate adjustor 81. On the rotating block 71, there is further provided a blood collection tube grasping means including a pair of arms 73 which are supported such that these shafts are rotated in mutually opposite directions by means of a fifth motor 120 which is also arranged on the block 71. When the fifth motor 120 is driven in a first direction, the arms 73 are rotated in such directions that distal ends of the arms are separated from each other so that a distance between the distal ends becomes large, but when the fifth motor 120 is driven in a second direction, the distal ends of the arms 73 become closer to each other so that the distance becomes small. Each of the arms 73 comprises a pin 73a at its middle point and a distal end portion of the arm can rotate about the pin with respect to the remaining portion, and there is arranged a coiled spring on the pin such that the distal end portion of the arm is biased to rotate in such a direction that the distal end portions come closer to each other. It should be noted that this rotational movement of the distal end portion of the arm due to the coiled spring is restricted by a suitable stopper not shown. When the fifth motor 120 is driven in the first direction and the arms 73 are separated from each other by a maximum length, a distance between the distal ends of arms is longer than an outer diameter of main body 51 of the blood collection tube 50, so that the arms 73 can grasp the tube.

Now the operation of the sample delivery apparatus of the present embodiment will be explained. It is assumed that the base member 111 is in a home position in which the nozzles 53 and 54 are situating above the washing vessel 107 and the arms 73 are in the opened condition. It should be noted that the nozzles 53 and 54 have been washed in the last sample delivery process. When a command for delivering a sample blood contained in a blood collection tube 50 placed in the first rack 102 as shown in FIG. 5 is produced from the control unit based on a preliminarily read signal of the bar code L, the motor 119 is driven in the first direction so that the base member 111 is moved leftward until the nozzles 53 and 54 situate above the relevant blood collection tube 50 in the first rack 102. Then, the motor 115 is driven in the second direction to descend the base member 111, slide member 116 as well as the block 71 to such a level that an upper portion of the blood collection tube 50 is inserted between the distal ends of the arms 73. After that, the motor 120 provided on the block 71 is driven in the second direction to move the distal ends of the arms 73 closer to each other and the blood collection tube 50 is clamped therebetween. Then, the motor 115 is driven in the first direction to move the base member 111, slide member 116 and block 71 upward until the blood collection tube 50 clamped between the arms 73 is removed from the rack 102. Next, the motor 119 is driven in the second direction to move the slide member 116 and all components provided on the slide member in the right direction such that the clamped blood collection tube 50 situates above the third rack 106. Then, the motor 115 is driven in the second direction to move the base member and all components provided on the base member downward until the blood collection tube 50 is inserted into the third rack 106. In this manner, the blood collection tube 50 can be transported from the first rack 102 to the third rack 106. The motor 115 is continuously driven in the second direction and the suction nozzle 53 and air supply nozzle 54 are inserted into the cap 52 made of rubber until tips of these nozzles penetrate through the cap. During this downward movement of the block 71, the motor 120 is driven in the first direction to move the pins 73a away from each other and thus angle formed by upper and lower arm portions about the pins 73a are decreased.

Figure 6:
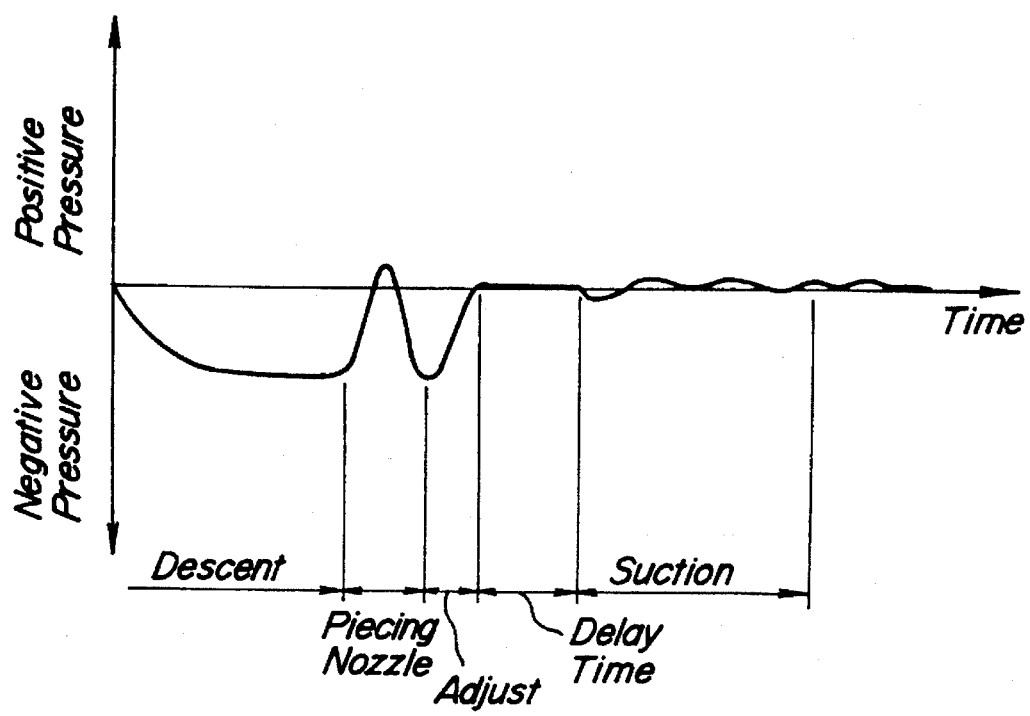
FIG. 6 is a graph representing a change of a pressure within the container.

Next, the motor 115 is driven in the first direction such that the blood collection tube 50 is lifted until a whole of the blood collection tube 50 is completely detached from the rack 106, and then the motor 76 is driven in the first direction to rotate the block 71 in the upward clockwise direction, so that the blood collection tube 50 is substantially turned over together with the block 71 in a dangling state in which a bottom of the main body 51 is free in an air and the cap 52 is supported by the nozzles 53 and 54. During the rotation, the blood collection tube 50 is stabilized by the arm 73 to reduce a mechanical burden which may be loaded on the nozzles 53 and 54. The rotation angle may be set to a value within a range from 120° to 150°, preferably about 135°. When the rotation angle is more than 150°, it may be happened that the bubbles are generated in the serum because of its turbulent flow, resulting in insufficiency of an amount of the serum sucked by the suction nozzle 53. It should be noted that this rotation has to be performed within a relatively short time period shorter than 2 seconds and more particularly shorter than one second by controlling an activation time of both the motor 62 and the motor 76. After 0.5 to 3 seconds, preferably 1 to 2 seconds after the blood collection tube 50 has been turned upside down, the motor 62 is driven to initiate the suction operation. It should be noted that during this time delay, the serum S completely descends and any possible air bubbles may be removed. Like as the first embodiment, during the sucking operation, the pressure inside the blood collection tube 50 is monitored by the pressure sensor 78 and the air supply from the air compressor 64 into the blood collection tube 50 by means of the air supply nozzle 54 is controlled. That is to say, the operation of the decompression valve 80 and air supply rate adjuster 81 is controlled by the control unit not shown in accordance with the detected pressure within the blood collection tube 50. A variation of the pressure inside the blood collection tube 50 is illustrated in FIG. 6.

After sucking a given amount of the serum S from the blood collection tube 50, the motor 62 is deenergized to stop the movement of the piston 60a of syringe 60. Then, the motor 76 is driven in the second direction to rotate the block 71 in the downward counter-clockwise direction such that the blood collection tube 50 stands upright. Then, the motor 115 is driven in the second direction to descend the base member 111 and all components provided on the base member are moved downward and the blood collection tube 50 is inserted into the third rack 106. Next, the motor 115 is driven in the second direction to move the base member 111 upward and at the same time the motor 120 is driven in the first direction to move the arms 73 such that the pins 73a are moved close to each other. Therefore, the suction nozzle 53 and air supply nozzle 54 are removed from the cap 52. This condition is identical with that shown in FIG. 5. After that the motor 115 is continuously driven in the second direction to remove the blood collection tube 50 from the third rack 106. Next, the motor 119 is driven in the first direction until the blood collection tube 50 comes into a position above the first rack 102 from which the relevant tube has been removed. Then, the motor 115 is driven in the second direction to move the base member 111 and all components provided on the base member such that the blood collection tube 50 is inserted into the first rack 102. The blood collection tubes from which the serum samples have been taken out may be transported into a waste tube treating position located at a downstream position of the first blood collection tube feeding path of the feeding means 101 and may be removed from the first blood collection tube feeding path into a stocker.

Next, the motor 119 is driven in the second direction until the suction nozzle 53 situates above a sample vessel 105 arranged in the second rack 106. After that, the motor 62 is driven in the second direction to move the piston 60a into the syringe 60 to discharge a given amount of the sucked serum S into the sample vessel 105. When a given amount of the serum sample S has to be delivered into a plurality of sample vessels, the second feeding means 103 is driven to index a next vacant sample vessel into a sample delivery position and then the motor 62 is driven again in the second direction to deliver a given amount of the serum sample into the sample vessel. In this manner, the sucked serum sample S can be delivered into a plurality of sample vessels the number of which corresponds to the number of test items denoted for the relevant sample which test items should be analyzed with a plurality of analyzers having same or different mechanisms from each other. After delivery, the sample vessels 105 are further advanced by the sample vessel feeding means 103 and are divided into suitable groups on the basis of the test items by means of a dividing means not shown. Then, the thus divided sample vessels are set on a plurality of analyzers manually or automatically which respectively correspond to the groups in accordance with the denoted test items.

After the sucked sample serum has been delivered into one or more sample vessels, the motor 119 is driven again in the second direction such that the suction nozzle 53 and air supply nozzle 54 situate at a washing position above the washing vessel 107. Then, the motor 115 is driven in the second direction to move these nozzles 53 and 54 downward until they are immersed into the washing liquid 108. After that, the motor 62 is driven in the first and second directions at least once to wash the inner and outer walls of the suction nozzle 53 and at the same time, the outer wall of the air supply nozzle 54 is washed. It should be noted that the new washing liquid 108 may be supplied into the washing vessel 107 by means of a suitable washing liquid supply means not shown. Finally, the motor 115 is driven in the first direction to move the base member 111 and all components provided on the base member including the suction nozzle 53 and air supply nozzle 54 upward in the home position.

FIG. 6 is a graph showing a variation of the pressure within the blood collection tube 50 during the above mentioned sample delivery operation. As stated above, initially the blood collection tube 50 containing a sample blood is remained at a negative pressure. After the air supply nozzle 54 is inserted into the container main body 51 through the cap 52, but before turning over the blood collection tube 50, the air is supplied into the blood collection tube 50 by operating the air pump 64, so that the pressure within the container is increased toward the atmospheric pressure. The pressure inside the blood collection tube 50 is continuously monitored by the pressure sensor 78. Then, the tube 50 is turned upside down by driving the motor 76 in the first direction and then a delay time of 1 to 5 seconds is introduced prior to the sucking operation. During this delay time, the serum sample S can complete a flowdown along the inclined inner side wall of the container 51, because the pressure in the blood collection tube 50 is increased to the atmospheric pressure and the liquid surface of the serum sample becomes stable, so that any error in an amount of sucked serum can be avoided. Next, during the sucking operation, the air is supplied into the blood collection tube 50 in such a manner that the pressure inside the tube is substantially remained constant. Therefore, the sucking operation can be performed smoothly and a given amount of the sample serum S can be accurately sucked into the suction nozzle 53.

In the present embodiment, the blood collection tube 50 held in the third rack 106 is grasped by the arms 73 and is pulled out of the third rack 106. After that, the blood collection tube 50 is turned upside down by rotating the block 71 to which the suction nozzle 53 and air supply nozzle 54 are secured. Therefore, the block 71 operates to rotate both the blood collection tube 50 and nozzles 53, 54. In other words, in the present embodiment, it is no more necessary to provide separate mechanisms for rotating the blood collection tube 50 and the nozzles 53, 54.

Furthermore, in the present embodiment, when the nozzles 53 and 54 pierce the cap 52, the blood collection tube 50 is in the normal posture in which the cap situates at a top of the tube 50, and the nozzles are inserted into the tube 50 to such an extent that openings of the nozzles are remained in an air space between the liquid surface and the rear surface of the cap 52. In this condition, the air is supplied into the tube 50 by means of the nozzle 54 and the pressure within the tube is increased to the atmospheric pressure without introducing air bubbles in the serum sample S. When the blood collection tube 50 is turned upside down, the opening of the suction nozzle 53 situate just above the rear surface of the cap 52, so that a sufficiently large amount of the serum sample can be sucked.

Figure 7:
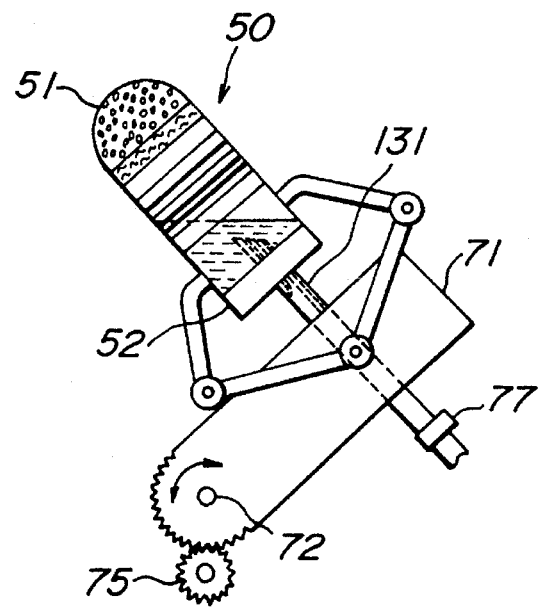
FIG. 7 is a schematic view illustrating another embodiment of the assembly of the nozzle.
Figure 8:
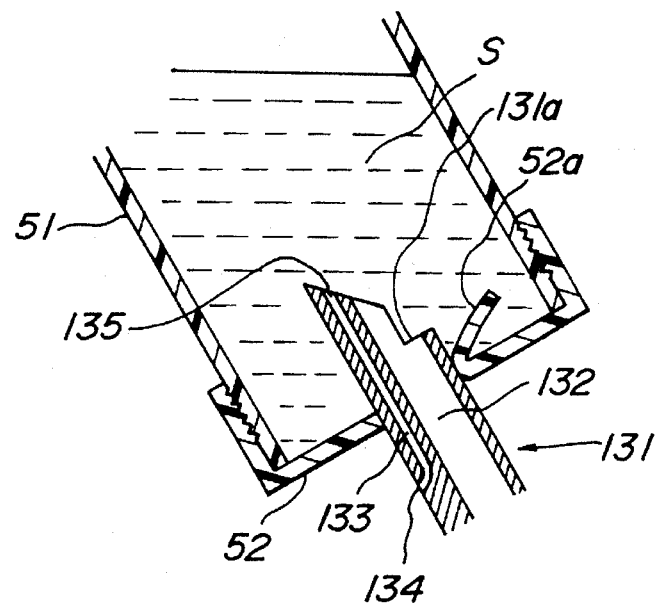
FIG. 8 is a cross sectional view showing a tip of the nozzle shown in FIG. 7 at an enlarged scale.

FIG. 7 is a schematic view showing another embodiment of an assembly of the suction nozzle and air supply nozzle. In the present embodiment, there is provided only one needle-like composite nozzle 131, and a sample sucking conduit 132 and an air supply conduit 133 are formed therein as clearly illustrated in FIG. 8. In FIG. 8, a tip of the needle-like composite nozzle 131 cut at an angle within a range from 20 to 40 degrees, particularly about 30 degrees.

If necessary, a resistance against the insertion of the tip of the nozzle 131 into the cap may be reduced by setting an insertion angle of the tip of the nozzle to a value near the above mentioned cut angle. The air supply conduit 133 is communicated with an air inlet 134 as well as with an air outlet 135. As shown in FIG. 7, when the needle-like composite nozzle 131 is inserted into the blood collection tube 50 through the cap 52 which is made of plastics and has a thickness of about 1 to 3 mm. The air inlet 134 is exposed to the surrounding atmosphere and the air outlet 135 is exposed in the sample serum S. The sample sucking conduit 132 is communicated with a sample inlet 136. A distance between the air outlet 135 and the sample inlet 136 is determined such that during the sucking operation, any air bubble introduced into the sample serum S from the air outlet 135 could not be sucked into the sample inlet 136 so that a predetermined amount of the sample serum S can be accurately sucked into the sample sucking conduit 132.

Furthermore, in the present embodiment, the cap 52 is made of plastics which is liable to be cut by the insertion of the nozzle. Therefore, in the present embodiment, a tip of the nozzle 131 is formed to have a step 131a having an angle of 90 degrees. Edges of the step 131a is rounded by sandblasting. When the tip of the nozzle 131 is inserted into the cap 52, a portion of the cap is cut and a cut portion 52a is bent inwardly. In this manner, the cut portion 52a is prevented from being separated from the remaining portion of the cap 52, and thus the cut portion could not affect the correct sucking operation. When the cap is formed by a plastic sheet such as polystyrene or polyethylene sheet having a thickness of 1 to 3 mm like as a sample transfer tube manufactured by Sarstedt company, a part of the cap might be punched out of the cap and falls into the serum sample. The fallen chip of the cap is liable to be sucked into the suction nozzle, so that the suction nozzle is clogged partially or completely. In the embodiment illustrated in FIG. 8, the tip of the nozzle 131 has the step 131a and the edge of the step is round off by the sandblasting, so that the cut portion 52a of the cap is not separated from the cap, so that it is possible to suck a required amount of the serum sample into the suction nozzle 131. A diameter of the composite nozzle 131 is about 1 mm or less and a portion of the cap made of plastics is cut sharply, so that there is formed a very small space between the nozzle and the cap and the serum sample could not flow through the small space due to the surface tension.

Figure 9:
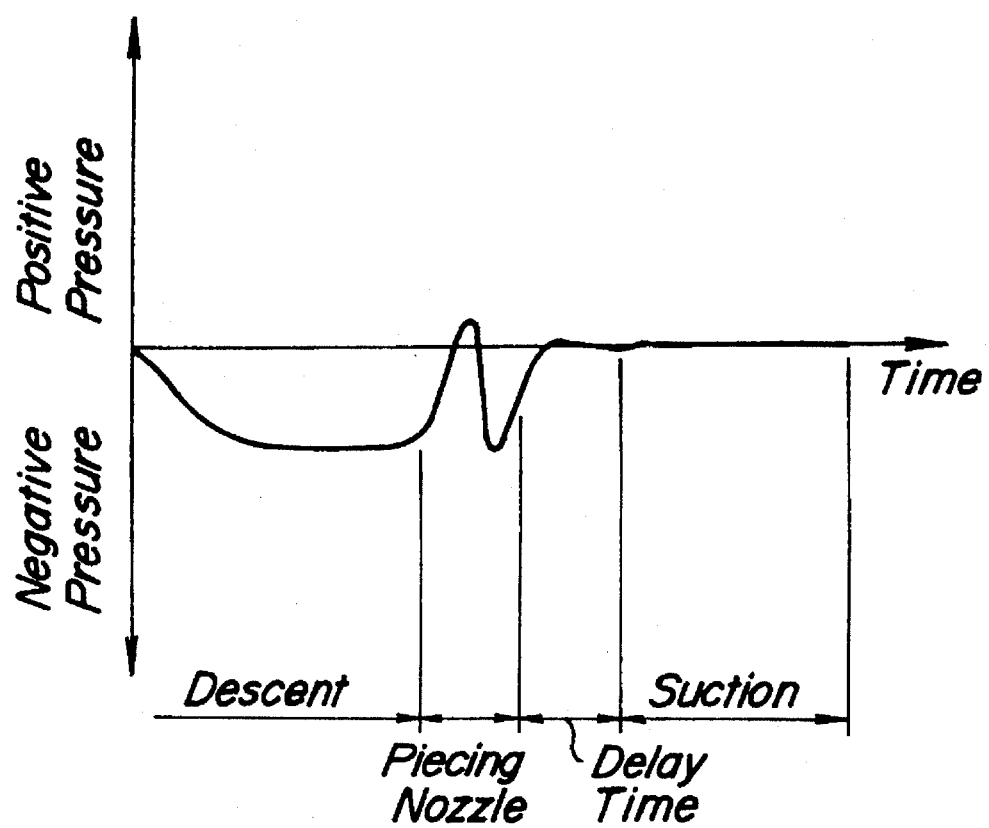
FIG. 9 is a graph representing a change of a pressure within the container.

FIG. 9 is a graph depicting a change in a pressure inside the blood collection tube 50 during the delivering operation of the present embodiment. At first, the pressure inside the blood collection tube 50 is at a negative pressure, and as soon as the needle-like member 131 is inserted into the blood collection tube by such an amount that the air outlet 135 is exposed from the cap 52, the pressure begins to increase toward the atmospheric pressure. When the Sample serum S is sucked into the sample sucking conduit 132, the air is introduced into the blood collection tube 50 by means of the air inlet 134, air conduit 133 and air outlet 135. Therefore, also in the present embodiment the sample sucking operation can be carried out smoothly and a given amount of the sample serum S can be sucked precisely. In the present embodiment, as soon as the composite nozzle 131 is inserted into the cap 52, the air is supplied into the blood collection tube 50 via the air supply conduit 133, so that it is no more necessary to provide the air control mechanism 64, 80 and 81 shown in FIGS. 2 and 5.

As shown in FIG. 7, according to the invention, it is preferable to construct the apparatus such that the opening of the suction conduit 132 is inclined with respect to its longitudinal axis and the tip of the nozzle is inserted into the blood collection tube 51 by such a distance that the whole opening of the suction conduit is exposed out of the cap 52. In this case, the direction of the inclination is preferably set such that when the blood collection tube 51 is turned over, the front surface of the tip of suction conduit is substantially in parallel with the liquid surface of the serum S. Then, a fear that the suction conduit might suck the air can be minimized.

Figure 10:
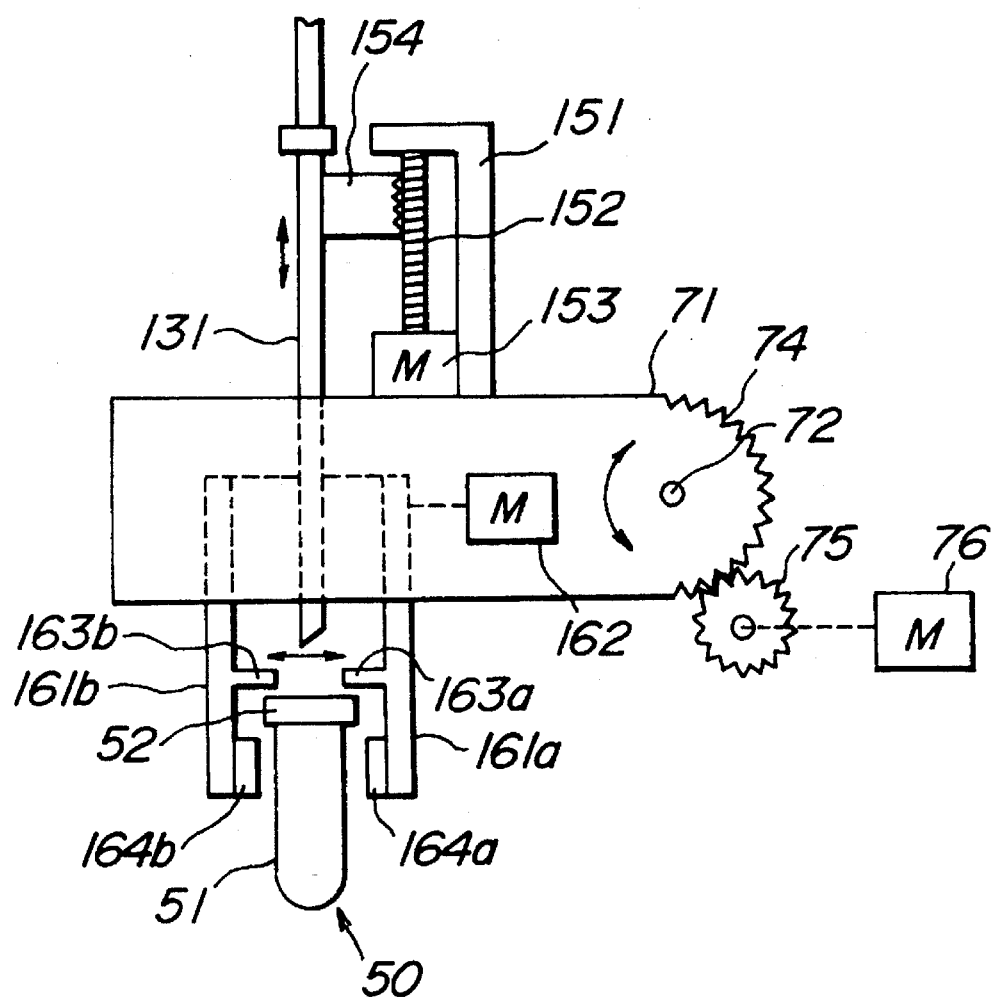
FIG. 10 is a schematic view showing an arm driving mechanism of another embodiment of the liquid content taking apparatus according to the invention.

FIG. 10 is a schematic view showing another embodiment of the liquid content taking apparatus according to the invention. In the above explained embodiments, the suction nozzle and air supply nozzle are secured to the block, so that the the piercing operation is carried out by descending the block 71. In the present embodiment, the composite nozzle 131 including the suction conduit 132 and air supply conduit 133 is provided on the block 71 movably up and down. To this end, the block 71 comprises an upright post 151, and an upright screw 152 which is rotated by a motor 153. To the composite nozzle 131 secured to the block 71 movably up and down there is secured a rack gear 154 which is engaged with the screw 152.

To the block 71 there are also provided a pair of arms 161a and 161b which are moved horizontally in mutually opposite directions by means of a motor 162. The arms 161a and 161b have inward projections 163a and 163b, respectively formed integrally therewith. On inner walls of tips of the arms 161a and 161b, there are arranged pads 164a and 164b, respectively. It should be noted that these pads 164a and 164b are made of resilient material such as rubber, so that they serve as cushion for positively grasping the main tube 51 of the blood collection tube 50. To this end, surfaces of these pads 164a and 164b are curved in correspondence upon an outer configuration of the main tube 51. The inward projections 163a and 163b are arranged on either or both of arms 161a and 161b so that they can be situated slightly above of the cap 52 when the arms 161a and 161b have grasped the main tube 51.

The operation of the present embodiment will be clear from the drawing and thus will be explained only briefly. Before descending the block 71, the arms 161a and 161b are separated from each other by driving the motor 162. The block 71 is moved downward such that the pads 164a and 164b face the side wall of the main tube 51 and inward projections 163a and 163b situate above a level of the cap 52. Then, the motor 162 is driven to move the arms 161a and 161b close to each other to grasp the main tube 51 by means of the pads 164a and 164b. Next, the motor 153 is driven to move the composite nozzle 131 downward to insert the tip of the nozzle into the blood collection tube 50 through the cap 52. The sample serum sucking and discharging operation is entirely identical with that of the previous embodiment. After delivering the sample serum and returning the blood collection tube into the home position, the motor 153 is driven in the opposite direction to remove the composite nozzle 131 from the cap 52. During this removal operation, the cap 52 can be effectively prevented from being pulled up together with the nozzle by means of the inward projections 163a and 163b.

The present embodiment is not limited only to the embodiments explained above, but many modifications and alternations may be conceived by those skilled in the art without departing the scope of the invention. For instance, in the above embodiments, the blood collection tube is stabilized by the arms during the rotation, it is not always necessary to grasp the tube by the arm, because a speed of the rotation can be easily restricken so as to prevent an undesired burden to the blood collection tube by controlling the motor 76. In this case the tube may be supported by one or more nozzles which are inserted into the cap made of rubber or plastics. Further, the piercing operation of the nozzle may be controlled by the output signal of the pressure sensor 78. That is to say, as soon as the tip of the nozzle has passed through the cap, the pressure sensed by the pressure sensor is changed, and this change in the pressure can be utilized to control the an amount of the penetration of the tip of the nozzle. In this manner, the tip of the nozzle can be correctly inserted into the cap such that the opening of the nozzle situates just under the rear surface of the cap although a thickness of the cap and a height of the blood collection tube vary. Alternatively, it is also possible to measure a height of the blood collection tube by means of a light beam sensor or to read out of the label applied on the blood collection tube, and the piercing operation may be controlled in accordance with the height of the tube. Moreover, the nozzles may be constructed such that they may be easily exchanged in accordance with kinds of samples and test items. Moreover, the blood collection tubes may be transported between the various racks by means of a mechanism having grasping arms or a belt conveyer to carry the first rack 102 to the position below the block 71 for piercing the cap 52 as shown in FIG. 5. In this case, not only the third rack 106 can be omitted, but also a time required for the movement of the block 71 between the position above the first rack 102 and the position above the third rack 106 can be saved. In the embodiment shown in FIG. 10, the inward protrusions 163a, 163b may be provided on a suitable moving member and may be driven into a position above the cap when the nozzle is removed from the cap. Moreover, when the third rack 106 shown in FIG. 5 is constructed to hold the blood collection tube 50 tightly, it is not necessary to support the blood collection tube by means of the arms during the piercing operation. It is also possible to arrange more than one nozzle set, so that a plurality of samples may be delivered simultaneously from more than one blood collection tube.

In the above embodiment, the blood collection tube is remained at a negative pressure so that the cap cannot be easily removed. However, in some blood collection tubes, the blood is collected at a low temperature under the atmospheric pressure. In such a case, when the tube is kept at a room temperature or is heated to a suitable reaction temperature, the pressure inside the tube is changed into a positive pressure. According to the invention, in such a case, after inserting the nozzle, the air may be sucked. In this manner, any error in a delivery amount due to the positive pressure may be avoided. In the embodiment depicted in FIG. 7, as soon as the composite nozzle 131 is inserted into the cap by a predetermined depth, the inside of the tube is communicated with the atmosphere, so that it is not necessary to perform any additional step of operation to the above description about FIG. 7. Moreover, in the above embodiments, the nozzle is inserted into the cap by descending the nozzle with respect to the blood collection tube, but according to the invention, it is also possible to move the blood collection tube upward with respect to the stationary nozzle or both the nozzle and tube may be moved close to each other by adding a means for lifting the tube such as an elevator device of the arms 73 or the third rack 106 shown in FIG. 5.

As explained above, in the sample delivery apparatus according to the invention, the sample liquid can be delivered effectively and accurately without performing the liquid level detection or the boundary layer detection, because the sample container is turned over before sucking the sample liquid. Further, it is not necessary to provide a liquid level detection system, and thus it is no more necessary to remove the bar code label from the blood collection tube in order to perform a liquid level detection by means of an optical device. Therefore, any possible error due to the removal of the bar code label from the blood collection tube can be effectively avoided.

What is claimed is:

1. An apparatus for taking a liquid content out of a container, said liquid content to be discharged into at least one liquid content receiving vessel for use in analysis, the container including a container main body having an opening and a cap which is hermetically secured to the opening to keep an inside of the container main body at an initial pressure, said apparatus comprising:

holding means for detachably holding said container in a normal posture in which the cap is at a top of the container;

liquid content taking means comprising at least a suction nozzle having a tip for piercing said cap and a hollow member with an opening in a vicinity of said tip to receive a liquid flow thereinto;

supporting means for supporting said liquid content taking means above said holding means and directing the tip of said suction nozzle downwardly towards said cap, while said container is being held by said holding means;

piercing means for moving said suction nozzle and said holding means selectively toward and away from each other such that said tip of said suction nozzle can be inserted into said cap until the opening of said hollow member protrudes from a rear surface of said cap into an inner space located between the rear surface of said cap and a surface of said liquid content, while said container is being held by said holding means, and further can be pulled out of the container main body through said cap;

rotating means for rotating said supporting means and said liquid content taking means while said suction nozzle is inserted into said cap, so that said container can be reversibly rotated together with the suction nozzle so as to change said normal posture into a sucking posture in which the container is substantially turned over and said cap is located at a bottom of said container;

transporting means for moving said liquid content taking means at least between a position above the cap of said container being held by said holding means and a position above at least a liquid content receiving vessel;

liquid content sucking and discharging means, communicated with said suction nozzle of said liquid content taking means, for sucking a required amount of the sample into said suction nozzle and for discharging a given amount of the sucked liquid content into said liquid content receiving vessel; and control means for controlling at least said piercing means, said rotating means, said transporting means and said liquid content sucking and discharging means.

2. An apparatus according to claim 1, wherein said liquid content sucking and discharging means comprises a syringe having a cylindrical main body coupled with the suction nozzle and a piston arranged movable within the main body and driving means for driving the piston.

3. An apparatus according to claim 2, wherein said driving means is operated intermittently such that given amounts of sucked sample are discharged intermittently into a plurality of liquid content receiving vessels.

4. An apparatus according to claim 1, wherein said suction nozzle is formed such that said opening of the nozzle is positioned on a plane which is inclined with respect to a longitudinal axis of the suction nozzle, and said piercing means is driven such that the suction nozzle is inserted into the inside of the container main body through the cap up to such a level that the whole opening of the suction nozzle is inserted through the cap.

5. An apparatus according to claim 1, wherein said liquid content sucking and discharging means comprises air supply nozzle for supplying air into the container main body through the cap.

6. An apparatus according to claim 5, wherein said air supply nozzle is arranged in parallel with the suction nozzle and is extended longer than said suction nozzle such that when the suction nozzle and air supply nozzle have been inserted into the container main body through the cap and the holding means has been rotated such that the container is inverted, the air supply nozzle is situated above a liquid level of the liquid content contained in the container main body.

7. An apparatus according to claim 6, wherein said rotating means rotates the container by an angle of 120° to 150°.

8. An apparatus according to claim 5, further comprising a means for detecting a sucking pressure provided between the suction nozzle and the sucking and discharging means.

9. An apparatus according to claim 1, further comprising a means for lifting said supporting means to detach the container from said holding means.

10. An apparatus according to claim 1, further comprising a means for stabilizing the container during the rotation by said rotating means.

11. An apparatus according to claim 5, wherein an inlet of said suction nozzle and an outlet of said air supply nozzle are spaced apart so as to avoid sucking of bubbles from said outlet of said air supply nozzle into said inlet of said suction nozzle.

12. An apparatus according to claim 1, further comprising a means for transporting said container from a pick-up position where a plurality of containers are fed one by one.

13. An apparatus according to claim 1, wherein said suction nozzle comprises a hollow needle.

14. An apparatus according to claim 13, wherein the tip of said suction nozzle is disposed on said hollow needle and is formed to have a step for preventing said suction nozzle from being separated from the cap of said container.

15. An apparatus for taking a liquid content out of a container, said liquid content to be discharged into at least one of a plurality of sample vessels for use in a plurality of analyzers, the container including a container main body having an opening and a cap which is hermetically secured to the opening to keep an inside of the container main body at an initial pressure, said apparatus comprising:

holding means for detachably holding said container in a normal posture in which the cap is at a top of the container;

liquid content taking means comprising at least a suction nozzle having a tip for piercing said cap and a hollow member with an opening in a vicinity of said tip to receive a liquid flow thereinto;

supporting means for supporting said liquid content taking means above said holding means and directing the tip of said suction nozzle downwardly towards said cap, while said container is being held by said holding means;

piercing means for moving said suction nozzle and said holding means selectively toward and away from each other such that said tip of said suction nozzle can be inserted into said cap until the opening of said hollow member protrudes from a rear surface of said cap into an inner space located between the rear surface of said cap and a surface of said liquid content, while said container is being held by said holding means, and further can be pulled out of the container main body through said cap;

rotating means for rotating said supporting means and said liquid content taking means while said suction nozzle is inserted into said cap, so that said container can be reversibly rotated together with the suction nozzle so as to change said normal posture into a sucking posture in which the container is substantially turned over and said cap is located at a bottom of said container;

transporting means for moving said liquid content taking means at least between a position above the cap of said container being held by said holding means and a position above at least a sample vessel;

liquid content sucking and discharging means, communicated with said suction nozzle of said liquid content taking means, for sucking a required amount of the sample into said suction nozzle and for discharging a given amount of the sucked liquid content into said sample vessel; and control means for controlling at least said piercing means, said rotating means, said transporting means and said liquid content sucking and discharging means.

16. An apparatus for taking a liquid content out of a container, said liquid content to be discharged into at least one of a plurality of sample vessels for use in a plurality of analyzers, the container including a container main body having an opening and a cap which is hermetically secured to the opening to keep an inside of the container main body at an initial pressure, said apparatus comprising:

holding means for detachably holding said container in a normal posture in which the cap is at a top of the container;

liquid content taking means comprising at least a suction nozzle having a tip for piercing said cap and a hollow member with an opening in a vicinity of said tip to receive a liquid flow thereinto;

supporting means for supporting said liquid content taking means above said holding means and directing the tip of said needle-like suction nozzle downwardly towards said cap, while said container is being held by said holding means;

piercing means for moving said suction nozzle and said holding means selectively toward and away from each other such that said tip of said suction nozzle can be inserted into said cap until the opening of said hollow member protrudes from a rear surface of said cap into an inner space located between the rear surface of said cap and a surface of said liquid content, while said container is being held by said holding means, and further can be pulled out of the container main body through said cap;

rotating means for rotating said supporting means and said liquid content taking means while said suction nozzle is inserted into said cap, so that said container can be reversibly rotated together with the suction nozzle so as to change said normal posture into a sucking posture in which the container is substantially turned over and said cap is located at a bottom of said container;

transporting means for moving said liquid content taking means at least between a position above the cap of said container being held by said holding means and a position above at least a reaction vessel;

liquid content sucking and discharging means, communicated with said suction nozzle of said liquid content taking means, for sucking a required amount of the sample into said suction nozzle and for discharging a given amount of the sucked liquid content into said reaction vessel; and control means for controlling at least said piercing means, said rotating means, said transporting means and said liquid content sucking and discharging means.

17. An apparatus according to claim 15, wherein said sample vessel is one of a plurality of liquid content receiving vessels, and wherein said driving means is operated intermittently such that given amounts of sucked sample are discharged intermittently into said plurality of liquid content receiving vessels.

18. An apparatus according to claim 16, wherein said reaction vessel is one of a plurality of liquid content receiving vessels, and wherein said driving means is operated intermittently such that given amounts of sucked sample are discharged intermittently into said plurality of liquid content receiving vessels.

19. An apparatus according to claim 15, wherein said rotating means rotates the container by an angle of 120° to 150°.

20. An apparatus according to claim 16, wherein said rotating means rotates the container by an angle of 120° to 150°.

21. An apparatus according to claim 15, further comprising a means for lifting said supporting means to detach the container from said holding means.

22. An apparatus according to claim 16, further comprising a means for lifting said supporting means to detach the container from said holding means.

\* \* \* \* \*